United States Patent [19]
Sebesta et al.

[11] Patent Number: 5,458,578
[45] Date of Patent: Oct. 17, 1995

[54] INFUSION PUMP TUBE

[75] Inventors: Kurt J. Sebesta, Huntington Beach; Kenneth W. Rake, Laguna Niguel, both of Calif.

[73] Assignee: I-Flow Corporation, Irvine, Calif.

[21] Appl. No.: 801,805

[22] Filed: Dec. 2, 1991

[51] Int. Cl.$^6$ .................................................. A61M 37/00
[52] U.S. Cl. ........................ 604/154; 604/153; 604/283; 604/905; 285/239
[58] Field of Search ................... 604/153, 154, 604/283, 905; 417/474, 475, 478; 285/921, 239, 240

[56] References Cited

U.S. PATENT DOCUMENTS

| | | | |
|---|---|---|---|
| 2,103,838 | 12/1937 | Bach | 285/921 |
| 2,985,469 | 5/1961 | Bowman, Jr. | 285/921 |
| 3,044,497 | 7/1962 | Rebut | 623/1 |
| 3,217,400 | 11/1965 | Illesy et al. | 285/921 |
| 3,582,234 | 6/1971 | Isreeli et al. | |
| 3,667,785 | 6/1972 | Kapeker | 285/921 |
| 3,899,198 | 8/1975 | Maroschak | 285/921 |
| 3,982,535 | 9/1976 | Bahrton | |
| 4,526,574 | 7/1985 | Pekkarinen | |
| 4,534,756 | 8/1985 | Nelson | |
| 4,650,471 | 3/1987 | Tamari | |
| 4,685,902 | 8/1987 | Edwards et al. | |
| 4,710,163 | 12/1987 | Butterfield | |
| 4,874,359 | 10/1989 | White et al. | |
| 4,929,236 | 5/1990 | Sampson | 604/283 |
| 4,936,760 | 6/1990 | Williams | |
| 4,969,670 | 11/1990 | Bonnema et al. | 285/921 |
| 4,969,879 | 11/1990 | Lichte | 604/283 |
| 4,979,940 | 12/1990 | Bobo, Jr. et al. | |
| 5,011,378 | 4/1991 | Brown et al. | |
| 5,018,945 | 5/1991 | D'Silva | |
| 5,026,348 | 6/1991 | Venegas | |
| 5,129,887 | 7/1992 | Euteneuer et al. | 604/283 |
| 5,180,197 | 1/1993 | Thompson, Jr. | 285/921 |
| 5,195,993 | 3/1993 | Gianakos | 604/905 |

FOREIGN PATENT DOCUMENTS 0454883  1/1951  Italy .................................. 285/239

OTHER PUBLICATIONS

Hawley's Condensed Chemical Dictionary, 11 Ed. (1987), p. 1018.

Primary Examiner—Paul Prebilic
Attorney, Agent, or Firm—Robert M. Asher

[57] ABSTRACT

A fluid administration set with an infusion pump tube having indentations near its ends within its inner cylindrical wall. The indentations are preferably V-shaped annular grooves. Each groove engages an annular barb on a hollow fitting. The hollow fittings have base members for engaging retaining walls in the pump set apart from one another at a precise predetermined distance. The outer circumference of the infusion pump tube is enlarged in the area of the indentation. Tabs are provided on the hollow fitting assembly for securing the administration set against the infusion pump. The set may include a pressure dome for occlusion sensing on one of the hollow fitting assemblies.

7 Claims, 2 Drawing Sheets

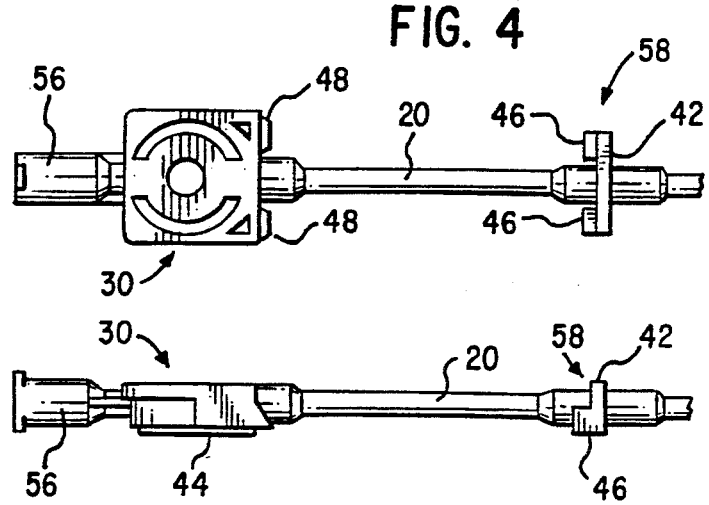
FIG. 4
FIG. 5
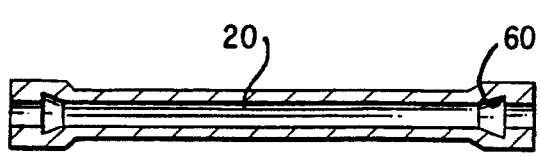
FIG. 6
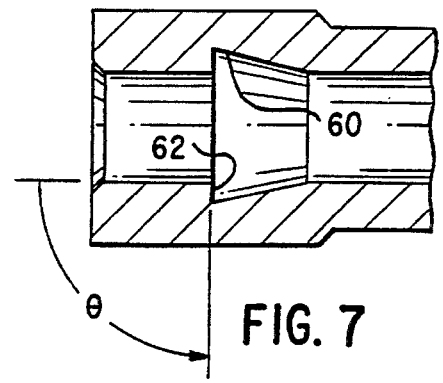
FIG. 7
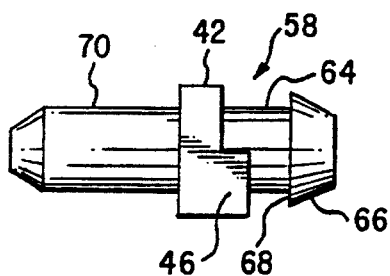
FIG. 8
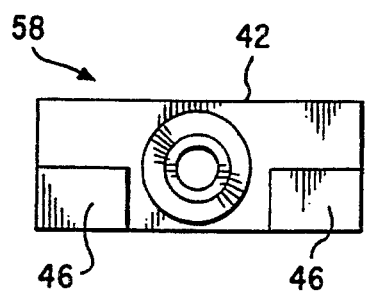
FIG. 9

INFUSION PUMP TUBE

BACKGROUND OF THE INVENTION

The present invention is directed to an infusion pump tube for use in a positive displacement infusion pump.

Positive displacement pumps for the infusion of parenteral medical fluids are generally characterized by a length of flexible tubing which is acted upon by one or more pumping elements. A rotary mechanism such as a cam shaft is generally used to reciprocate the pumping elements. The flexible tubing is generally disposed between the pumping elements and an opposing platen. The particular infusion pump described herein utilizes two valves and an expulsor as the pumping elements.

One valve serves as an inlet and the other as an outlet. The expulsor serves to compress the flexible infusion pump tube and expel fluid. When the expulsor is retracted from the pump tube, the tube returns to its substantially round uncompressed position. In operation, the inlet valve opens to allow fluid into the tube with the expulsor retracted. To expel fluid, the inlet valve closes, the outlet valve opens and the expulsor is moved against the tube to fully compress it.

An important factor in the accuracy of the fluid delivered by such a pump is the dimension of the infusion pump tube which is acted upon by the expulsor. The volume of fluid expelled by the expulsor is closely approximate to the area of the substantially round internal passageway of the pump tube times the length of the expulsor. Thus, any variation in the manufacturing process which affects the area of the substantially round internal passageway of the tube will affect the volume of fluid expelled. Furthermore, mounting of the tube within the pump in a manner which varies the stretching of the tube from pump to pump will also affect the effective area of the internal passageway thereby affecting the volume of fluid expelled.

A method of mounting a pump tube within an infusion pump is disclosed in U.S. Pat. No. 5,011,378 (Brown et al.). Brown et al. discloses a pump tube mount with a cylindrical fitting having an annular groove around its exterior surface. A pump tube mounted on this fitting is held in place by a collar placed over the tube concentrically aligned with the groove. The pump tube mount includes a rear wall with a pair of tabs for holding the mount in place within an infusion pump.

The object of the present invention is to start with a precisely manufactured tube and mount it into an infusion pump in a manner such that the dimensions of the tube are repeatable.

SUMMARY OF THE INVENTION

The present invention is directed to a hollow elastic infusion pump tube. The ends of the pump tube are used for attachment onto a cylindrical fitting. The inner cylindrical wall of the pump tube in the attachment portion is formed with indentations, preferably in the form of a V-shaped annular groove. The pump tube is preferably molded. The outer circumference of the pump tube is enlarged at the ends in the area of the indentations. The fitting for insertion into the end of the pump tube has a retaining member preferably in the form of an annular barb which engages the indentation on the inner circumference of the pump tube to prevent the tube from pulling away from the hollow fitting. The combination of the barb and the groove advantageously maintain the tube in a repeatable position. This avoids irregular stretching of the tube from one pump to another thereby providing a better tolerance as to the nominal volume of fluid pumped by the expulsor against the pump tube.

The hollow fittings are formed on a base member. The base members on opposite ends of the pump tube are set a fixed distance apart by retaining walls precisely positioned on the pump. Each base member includes a number of tabs so that an overhang portion on the retaining wall may be used to engage the tabs and hold the fitting assemblies down against the pump.

Other objects and advantages of the present invention will become apparent from the following description of the presently preferred embodiment taken in conjunction with the drawings.

BRIEF DESCRIPTION OF THE DRAWINGS

FIG. 4 is a plan view of a fluid administration set of the present invention.

FIG. 5 is a side view of the fluid administration set of FIG. 4.

FIG. 6 is a cross-sectional view of an infusion pump tube of the present invention.

FIG. 7 is a blown up cross-sectional view of an end portion of the pump tube of FIG. 6.

FIG. 8 is a side view of a mounted hollow fitting of the present invention.

FIG. 9 is an end view of the fitting of FIG. 8.

DETAILED DESCRIPTION OF THE PREFERRED EMBODIMENT

Figure 1:
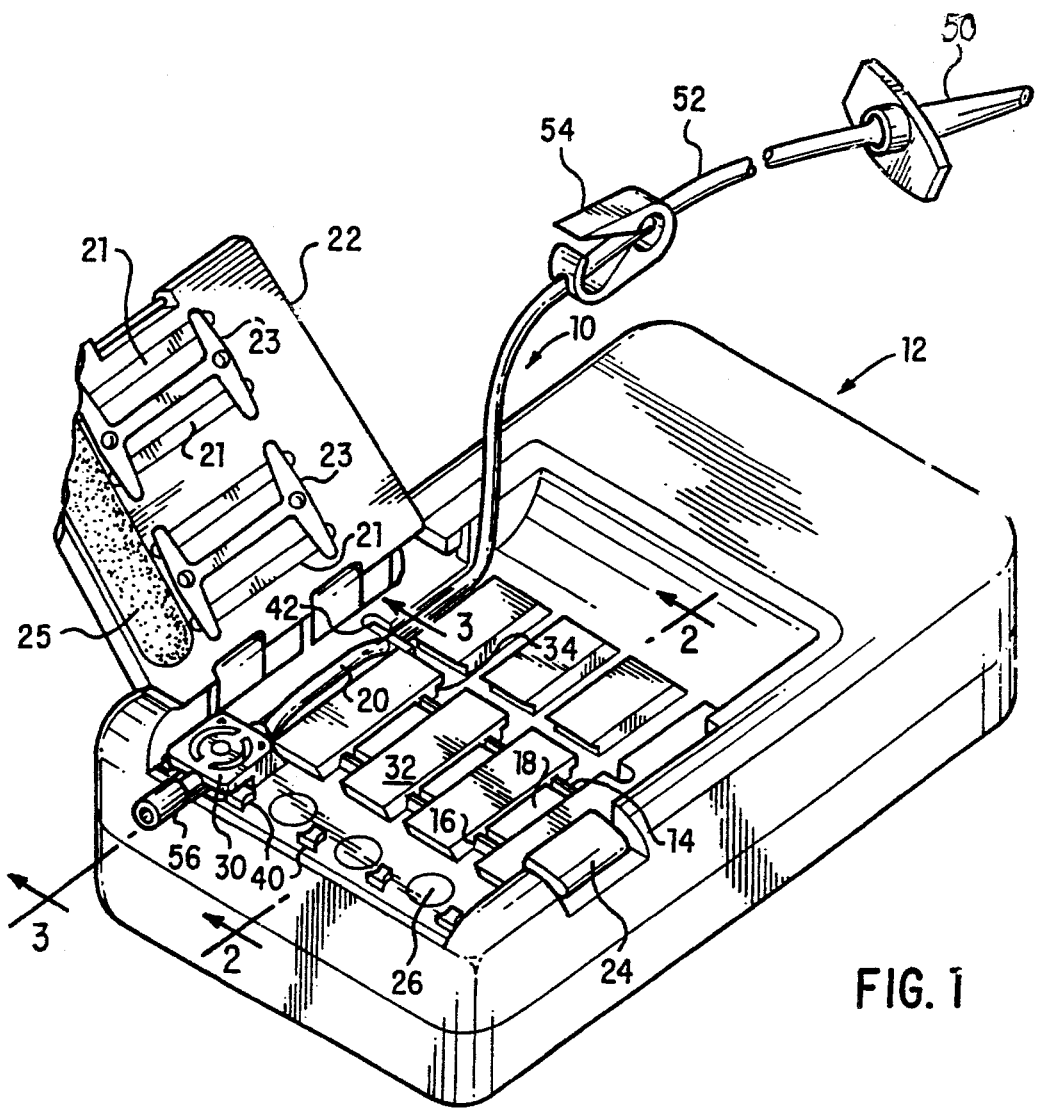
FIG. 1 is an isometric view of a positive displacement infusion pump with an infusion pump tube set of the present invention.

Referring now to FIG. 1, a fluid administration set 10 of the present invention is shown inserted into a positive displacement infusion pump 12. The pump 12 shown in FIG. 1 can accommodate four fluid administration sets for separately pumping four fluids. The pumping elements provided by the infusion pump 12 include an inlet valve 14 and an outlet valve 16 and an expulsor 18. Each of the four pumps contained in the infusion pump 12 includes all three of these pumping elements. These pumping elements are operated in a conventional manner by a cam shaft within the infusion pump. Initially, the outlet valve 16 compresses an infusion pump tube 20 against a platen 21. In the pump shown in FIG. 1, the platen 21 is carried on a door which latches closed upon the pump tubes by use of the latch 24. With the outlet valve 16 closed and the expulsor 18 and inlet valve 14 retracted, fluid fills the infusion pump tube 20. Then the inlet valve 14 compresses the pump tube 20. The outlet valve 16 is retracted and the expulsor 18 is pushed against the pump tube to expel the fluid from the tube and out into a catheter line to a patient.

The platen 21 is a layer of high shore hardness rubber lying in a same shaped groove in the door. The platen 21 is made of polyurethane in the presently preferred embodiment. The platens for each channel are held on the door by an I-shaped retainer 23. The distance between the platens and the pumping elements are set by the latch 24. When the pumping elements push against the platens on the door, it is the latch which prevents the door from being pushed back more than a preset distance from the pumping elements.

The infusion pump 12 shown in FIG. 1 is also provided with a pressure transducer 26 in each pumping channel line for occlusion sensing. A pressure dome 30 is provided with the fluid administration set so that the pressure of the fluid in the administration set can be monitored by the pressure transducer 26. Fluid output from the pumping elements into the pressure dome 30 spreads out over the circular surface of a diaphragm 44. The present diaphragm is preferably a PVC film welded to the bottom side of the pressure dome 30. The pliable plastic diaphragm will expand as fluid pressure builds up. The diaphragm is positioned adjacent the pressure transducer. The pressure transducer 26, thus, monitors the fluid pressure against the diaphragm in a conventional manner to determine whether an occlusion is present in the infusion line.

Figure 2:
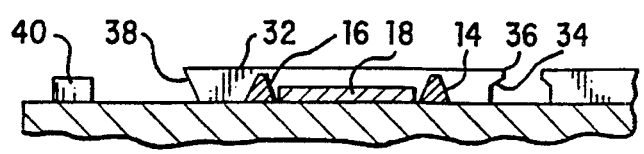
FIG. 2 is a partial cross-sectional view of the infusion pump of FIG. 1.

In between each of the pumping channels of the infusion pump 12 there are a series of elevated surfaces 32 separating the channels. The ends of the elevated surfaces 32 include retaining walls that are used to precisely fix the distance between the ends of the infusion pump tube when it is inserted in the pump. The retaining walls are located beyond the ends of the pumping elements. At the inlet end, the retaining wall 34 is provided with an overhang portion 36 as best seen in FIG. 2. Also at the outlet end of the spacer, the retaining wall 38 is oriented so that the top of the wall overhangs the lower portion of the wall. These overhanging portions in the retaining walls are used in conjunction with the fluid administration set 10 to hold the set down against the pump. The pump also includes pressure dome retaining members 40 which assist in positioning the pressure dome over the diaphragm 26. A low shore hardness rubber layer 25 is positioned on the door 22 so as to align with the pressure domes 30. The rubber layer 25 acts like a spring so as to push the pressure domes down against the transducers when the door 22 is closed.

Figure 3:
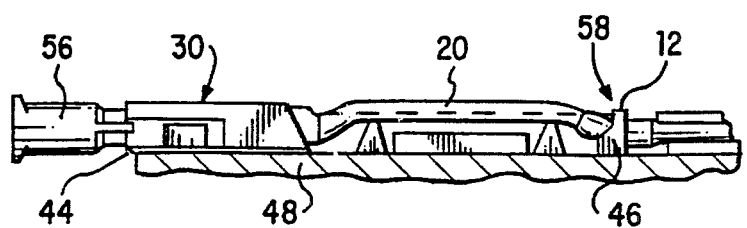
FIG. 3 is a partial cross-sectional view of the pump tube set of the present invention within the infusion pump of FIG. 1.

As shown in FIG. 3, the infusion pump tube 20 is attached between a base member 42 and a pressure dome 30. However, the present invention can be made with two base members similar to base 42 if a pressure dome 30 as in the preferred embodiment is not required. The body of the pressure dome 30 acts as a base for a fitting to be attached at one end of the infusion pump tube. The base member 42 includes a pair of tabs 46 which extend out from the base member 42 in a direction towards the infusion pump tube 20. The tabs 46 fit snugly beneath the overhang portion 36. The base member 42 is thus prevented from pulling up away from the infusion pump by the engagement of the tabs 46 with the overhang portion 36. Likewise, at the outlet end of the pump tube, the base of pressure dome 30 has an extending tab portion 48 which fits beneath the overhang formed by the retaining wall 38. The engagement of the overhanging retaining wall 38 and the extension tab 48 maintains the outlet side of the pump tube down in position against the infusion pump. The tabs 46 and tab 48 are thus aligned in a plane parallel to the infusion pump tube beneath the overhangs in their respective retaining walls.

The fluid administration set 10 of the present invention shall now be discussed in greater detail in FIGS. 4 and 5. At the inlet end of the administration set, a spike 50 is used for insertion into a fluid source pouch for accessing the fluid therein. The fluid is conducted through a PVC input tube 52. A tube clamp 54 is provided on the tube for stopping fluid flow from the fluid source pouch. Referring now to FIGS. 4 and 5, the input tube 52 is solvent bonded to one end of a first fitting assembly 58. The first fitting assembly 58 used on the input end is comprised of the base member 42 and has hollow fittings on opposite sides of the base member 42. One fitting is inserted into the input tube. The opposite fitting is inserted into the infusion pump tube 20 of the present invention. The other end of the infusion pump tube 20 fits over a fitting extending from a second fitting assembly including the pressure dome 30. The fitting extends from the base of the pressure dome 30. At the opposite end of the pressure dome 30, an outlet luer fitting 56 is provided for engagement with a patient administration line.

Referring now to FIGS. 6 and 7, the infusion pump tube 20 of the present invention shall be discussed in greater detail. The infusion pump tube is preferably perfectly elastic. Since a perfectly elastic material is not known, the presently preferred material is silicone rubber. Silicone rubber is more elastic than flexible PVC tubing. Since the PVC tubing is less expensive, it is used for the input tube 52. The infusion pump tube 20 and the PVC input tube 52 are connected by the fitting assembly 56.

Each end of the infusion pump tube 20 attaches to a hollow fitting. In accordance with the present invention, the attachment portions at the ends of the infusion pump tube 20 are formed with an indentation in the inner cylindrical wall. The indentation should have an edge which cooperates with the retaining member on the hollow fitting to position the ends of the tube on the fitting. The preferred configuration of the indentation is in the form of a V-shaped annular groove 60. The groove 60 is located near the end of the infusion pump tube so that it may engage a barb on the fitting. The V-shaped groove forms an edge 62. While the shape of the groove 62 may vary, it is important to provide an edge 62 to retain the pump tube on the fitting. The edge 62 precisely positions the tube and prevents the tube from being pulled away from the fitting by the pumping action of the expulsor. Furthermore, it provides a ready indication to an assembler putting the tube onto the fitting when the groove snaps over the barb that the tube is sufficiently inserted onto the fitting. The edge 62 forms an angle theta with the inner cylindrical wall at the end of the infusion pump tube which is small enough to hold the tube securely on the fitting. The presently preferred angle is 90°. The edge prevents the tube from being pulled away from its predetermined position on the fitting. The engagement of the edge 62 in the V-shaped groove 60 with the barb of the fitting advantageously provides for repeatable positioning of the pump tube on the fittings. So that the indentation or groove does not create a weakness in the wall of the infusion pump tube, the outer circumference of the pump tube is enlarged at the ends of the tube in the area of the indentation.

In order to produce an accurate infusion pump tube with a precise distance between the edge 62 at either end of the tube, it is preferred that the tube be formed by molding. The mold accurately fixes the relative locations of the V-shaped grooves. The entire pump tube is integrally molded as a single unit.

To understand the contribution of the attachment method of the present invention to improving the accuracy of the infusion pump, one should consider the tubing when it is stretched. When a tube is stretched, the internal diameter of the tube decreases. Thus, the area of the substantially round internal passageway decreases resulting in a decreased stroke volume for the expulsor. If the amount of stretch remains constant for all tubes that are inserted into the pump, then flow accuracy errors can be minimized. If, however, the amount of stretch varies from tube to tube depending on where the pump tube has been located on its fittings, the product will experience flow accuracy shifts from administration set to administration set. The present invention advantageously provides for repeatable axial placement of the infusion pump tube on its associated fittings.

The fittings used in the present invention are more particularly described with respect to FIGS. 8 and 9. The fitting assembly 56 is hollow to include a passageway for the flow of fluid from one tube to another. The fitting assembly 58 is provided with a base member 42 for butting up against a pair of retaining walls on either side of the infusion pump channel. The distance between the retaining walls is precisely machined. The base members are thus precisely positioned relative to one another when inserted in the pump. The length of the infusion pump tube and the distance between the V-shaped grooves therein should be predetermined so that there is some stretch in the tube when the base members of the hollow fittings at either end are up against their respective retaining walls. The slight stretching of the infusion pump tube when the fittings are in place within the pump can be identically repeated by each administration set. Advantageously, this provides for minimal deviation in the stroke volume from one administration set to another.

Extending from the base members 42 in the direction of the infusion pump tube are a pair of tabs 46. The tabs 46 straddle a neck 64 which extends out from the center of the base member 42. Each tab 46 is used to engage the overhanging portion of the retaining wall on either side of the infusion pump tube. A hollow fitting includes neck 64 and a retaining member extending radially out from the neck. In the preferred embodiment, the retaining member is an annular barb 66. The barb has a rear edge 68 which, when inserted into an infusion pump tube 20, butts against the edge 62 within the infusion pump tube 20. The positioning of the edge 62 of the tube against the edge 68 of the barb prevents the infusion pump tube 20 from being pulled away from the neck 64 of the fitting assembly. The outer end of the neck 64 is narrowed and expands gradually to the barb 66 so that the infusion pump tube can be easily guided onto the neck. On the opposite side of the base member 42 from the neck 64 is a second neck 70 for insertion into the incoming tube 52. The neck 70 is solvent bonded to the input tube 52.

At the output of the fluid administration set, the fitting assembly is formed with the pressure dome 30 thereon. A pair of tabs 48 extending from the base of the dome 30 engage their respective retaining walls 38. At the opposite end of the pressure dome from the neck of the fitting, there is an output luer fitting 56 for attachment to an infusion line.

Of course, it should be understood that various changes and modifications to the preferred embodiment described above will be apparent to those skilled in the art. For example, the fluid administration set of the present invention may be used with a variety of positive displacement pumps including multifinger peristaltic pumps. Furthermore, the fittings assemblies may be configured in a variety of ways for accurate positioning within a pump depending on how the pump is constructed with respect to retaining walls or the like. Still further, the indentations on the inner wall of the pump tube may assume a variety of shapes including notches or semicylindrical channels so long as they serve to restrict movement when contacted with a retaining member of a hollow fitting. These and other changes can be made without departing from the spirit and scope of the infusion pump tube invention and without diminishing its attendant advantages. It is therefore intended that such changes and modifications be covered by the following claims.

We claim:

1. An infusion pump tube set comprising:

an elongated hollow pump tube having an inner wall with an indentation on said inner wall near each of two ends of said tube;

a first hollow fitting assembly including two necks extending in opposite directions from a base member, one of said necks having a retaining member extending radially therefrom, said retaining member engaging the indentation in one of the ends of said hollow pump tube;

a second hollow fitting assembly having a neck extending from a base member, the neck having a retaining member extending radially therefrom, said retaining member engaging the indentation in the other of the ends of said hollow pump tube; and a pressure dome attached to the base member of said second hollow fitting opposite from the neck of said second hollow fitting assembly.

2. The infusion pump tube set of claim 1 further comprising tabs extending out from each of said base members in the direction of said hollow pump tube, all of said tabs being oriented in a plane parallel to said hollow pump tube.

3. The infusion pump tube set of claim 1 wherein the indentation in each of the ends of said hollow pump tube comprises a V-shaped annular groove.

4. The infusion pump tube set of claim 3 wherein the inner wall of said pump tube which extends to the end of said pump tube forms an angle with said V-shaped groove sufficiently small to maintain said pump tube in position on said retaining member.

5. The infusion pump tube set of claim 3 wherein each of said retaining members comprises an annular barb around the neck from which said each retaining member extends.

6. The infusion pump tube set of claim 1 wherein said hollow pump tube is formed by molding.

7. The infusion pump tube set of claim 1 wherein said hollow pump tube has an enlarged outer circumference near its ends about the indentations.

\* \* \* \* \*